United States Patent [19]
Crathorne et al.

[11] 3,975,299
[45] Aug. 17, 1976

[54] PRODUCTION OF ACID HYDROCARBON CONVERSION CATALYSTS

[75] Inventors: Elizabeth Anne Crathorne, Surbiton; Ian Valentine Howell, Woking; Robert Chalmers Pitkethly, Camberley, all of England

[73] Assignee: The British Petroleum Company Limited, London, England

[22] Filed: June 10, 1974

[21] Appl. No.: 477,841

[30] Foreign Application Priority Data
June 14, 1973  United Kingdom............. 28331/73
Aug. 30, 1973  United Kingdom............. 40786/73

[52] U.S. Cl................. 252/432; 252/437; 252/439; 252/441; 252/442; 260/683.47; 260/683.65; 260/683.68; 260/683 D; 208/120
[51] Int. Cl.²................. B01J 27/02; B01J 27/12
[58] Field of Search........... 252/437, 441, 442, 439, 252/432

[56] References Cited
UNITED STATES PATENTS

| | | | |
|---|---|---|---|
| 2,999,074 | 9/1961 | Bloch et al.......................... | 252/442 |
| 3,121,696 | 2/1964 | Hoekstra............................. | 252/441 |
| 3,144,414 | 8/1964 | Silverman........................... | 252/437 |
| 3,285,878 | 11/1966 | MacKenzie...................... | 252/441 X |
| 3,385,797 | 5/1968 | Bloch et al......................... | 252/439 |
| 3,590,025 | 6/1971 | Tittle.................................. | 252/437 X |
| 3,651,163 | 3/1972 | Radford et al................... | 252/432 X |
| 3,678,120 | 7/1972 | Bloch................................ | 252/441 X |
| 3,817,931 | 6/1974 | Brooks et al..................... | 252/442 |
| 3,824,180 | 7/1974 | Hilfman........................... | 252/439 X |
| 3,852,184 | 12/1974 | Siskin et al..................... | 252/441 X |

*Primary Examiner*—Patrick P. Garvin
*Attorney, Agent, or Firm*—Morgan, Finnegan, Pine, Foley & Lee

[57] ABSTRACT

A process for the production of a solid acidic catalyst which process comprises reacting a compound of formula $XF_5$ wherein X is phophorus, arsenic, antimony, bismuth, tantalum, vanadium or niobium with an inorganic oxide containing surface hydroxyl groups and having an Ho valve of less than —3.0. In a preferred embodiment alumina is partially fluorinated or sulphonated prior to reaction with the compound $XF_5$, in which X is preferably antimony.

14 Claims, No Drawings

PRODUCTION OF ACID HYDROCARBON CONVERSION CATALYSTS

The present invention relates to the preparation of solid acidic catalysts and to hydrocarbon conversion processes employing such catalysts.

The preparation of super acidic catalysts by the reaction of a Group V metal fluoride e.g. $SbF_5$ with hydrofluoric and fluorosulphonic acids has been previously described and their use for the isomerisation, alkylation and cracking of hydrocarbons has been proposed. However these catalysts are homogeneous and their recovery from the reaction mixture is therefore difficult.

U.S. Pat. No. 3,394,202 describes the production of a heterogeneous catalyst by impregnating an inert fluorided alumina support with hexafluoroantimonic acid prepared from a mixture of hydrogen fluoride and antimony pentafluoride. The specification stresses that the term "inert" as applied to support materials means that the carrier material does not substantially react with the hexafluoroantimonic acid. This does not necessarily require that the support material be intrinsically inert but that non-inert solids be treated to make them inert e.g. by coating with a thin layer of inert material. Thus non-inert porous solids useful as supports are subjected to a passivation treatment rendering the support inert to hexafluoroantimonic acid prior to impregnation therewith.

In the present invention solid acidic catalysts are prepared by reacting Group V metal fluorides directly with inorganic oxides containing surface hydroxyl groups.

Thus according to the present invention there is provided a process for the production of a solid acidic catalyst suitable for use in hydrocarbon conversion reactions which process comprises reacting a compound of formula $XF_5$ wherein X is phosphorus, arsenic, antimony, bismuth, tantalum, vanadium or niobium with an inorganic oxide containing surface hydroxyl groups and having an Ho value of less than —3.0.

The term Ho value is defined by H. A. Benesi in J. Amer. Chem. Soc. 1956, 78, 5490.

The inorganic oxide may be an oxide of an element of Groups II to VI, preferably of Groups III and IV, of the Periodic Table according to Mendeleef or a mixture of such oxides. Preferably the oxide is alumina, boria or mixtures thereof with silica.

The inorganic oxide employed may be derived from a heteropoly acid on a support by impregnating the support with a solution of the heteropoly acid followed by drying and then heating to drive off the water of crystallisation. A suitable support is silica. The product is believed to be a mixture of oxides highly dispersed on the support.

In order to lower the Ho value the inorganic oxide may be partially fluorinated before reaction with the compound of formula $XF_5$ e.g. by impregnation with ammonium fluoride followed by heating. Alternatively the inorganic oxide may be partially sulphonated by reaction with a sulphonating agent.

In a preferred embodiment of the invention alumina having surface hydroxyl groups is reacted with sufficient of a fluorinating or sulphonating agent to partially fluorinate or sulphonate the alumina, excess fluorinating or sulphonating agent is removed and thereafter the partially fluorinated or sulphonated alumina is reacted with the compound of formula $XF_5$ wherein X is phosphorus, arsenic, antimony, bismuth, tantalum, vanadium or niobium.

By partial fluorination is meant reaction of the alumina with less fluorinating agent than is required to convert the alumina completely to aluminium trifluoride. It is believed that partially fluorinating the alumina produces an alumina in which some, but not all, of the surface hydroxyl groups are replaced with fluorine. Correspondingly by partial sulphonation is meant reaction of the alumina with less sulphonating agent than is required to convert the alumina completely to aluminium sulphonate. It is believed that in partial sulphonation some, but not all of the hydrogen atoms, in the hydroxyl groups are replaced with $—SO_3H$ groups.

The alumina may be partially fluorided by treatment with hydrogen fluoride or ammonium fluoride followed by heating.

The alumina may be partially sulphonated by contact with chlorosulphonic acid ($HSO_3Cl$) or by sulphur dioxide in admixture with air or by sulphur trioxide. Also fluorosulphonic acid may be used but this compound is less effective as a sulphonating agent.

It is preferred to treat the partially fluorinated alumina with an inert gas at elevated temperature for a period after removing any unreacted fluorinating or sulphonating agent and prior to reacting the alumina with the compound of formula $XF_5$. A suitable treatment is to contact the partially fluorinated alumina with nitrogen at a temperature in the range 300° to 800°C for a period of 1 to 8 hours.

The alumina may be in any of its different crystalline forms although γ-(gamma)alumina or η-(eta-)alumina are preferred. Alternatively amorphous alumina may be used.

The alumina may be mixed with another inorganic oxide. Suitable inorganic oxides are boria and silica.

Preferably the extent of the partial fluorination or sulphonation is such that the alumina contains from 1 to 45%, more preferably 1 to 25%, even more preferably 5 to 25%, by weight of fluorine or from 1 to 20%, more preferably 2 to 12%, by weight of sulphur respectively.

A hydrogenating component e.g. a Group VIII metal may be present on the fluorinated or sulphonated alumina before contacting the alumina with the compound of formula $XF_5$. The hydrogenating component may be added to the alumina before or after partially fluorinating or sulphonating the alumina. Of the Group VIII metals which may be used as the hydrogenating component platinum is preferred in amounts from 0.01 to 5% by weight.

It is believed that the products of the reaction between the inorganic oxide and the compound of formula $XF_5$ contain units of the formula:

$—O—XF_5^-H^+$ and/or 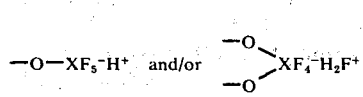

When the inorganic oxide is alumina it is believed that the $XF_5$ compound reacts with the surface hydroxyl groups of the alumina and that the reaction products contain units of the formula:

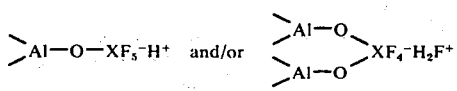

or in the case of the sulphonated alumina:

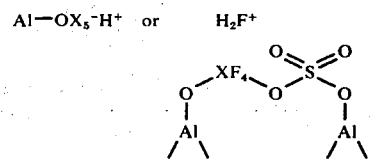

However the invention is not intended to be limited in any way by the aforegoing belief.

Preferably X in the compound of formula $XF_5$ is antimony.

The compound of formula $XF_5$ may be passed in the vapour phase over the inorganic oxide containing —OH groups or the partially fluorinated or sulphonated alumina or may be impregnated from solution in a solvent such as 1,1,2-trichlorotrifluoroethane. Alternatively the compound of formula $XF_5$ may be impregnated on to partially fluorinated alumina as a solution in sulphur dioxide.

The inorganic oxide or partially fluorinated or sulphonated alumina is preferably reacted with the compound of formula $XF_5$ at a temperature in the range −50° to +140°C, even more preferably 0° to +120°C.

The $Ho$ value of the inorganic oxide or the partially fluorinated or sulphonated alumina is preferably less than −8.0.

After reacting the compound of formula $XF_5$ with the inorganic oxide or the partially fluorinated or sulphonated alumina it is preferred to remove any excess of the compound $XF_5$. This is preferably effected by desorbing to constant weight at a temperature below 200°C, preferably at a temperature in the range 20° to 120°C.

It is preferred to activate the catalysts prepared by the methods hereinbefore described by treating the catalysts with isobutane, preferably with an excess of isobutane. Preferably any excess of isobutane is removed prior to using the catalyst in hydrocarbon conversion processes.

The invention also comprises the catalyst when prepared by a process as hereinbefore described.

The catalysts produced by the process as hereinbefore described may be used to catalyse a wide range of hydrocarbon conversion reactions which are catalysed by acidic catalysts e.g. alkylation, isomerisation, dealkylation, transalkylation, disproportionation and cracking.

Thus according to another aspect of the present invention there is provided a process for the isomerisation of hydrocarbons which process comprises contacting a hydrocarbon feedstock with a solid acidic catalyst produced by the process as hereinbefore described under isomerisation conditions.

Preferably the hydrocarbon feedstock is an n-paraffin or mixture of n-paraffins of carbon number 4 to 10 e.g. n-pentane and the isomerised product is an isoparaffin e.g. isopentane.

Preferably the isomerisation is effected at a temperature in the range −20° to +100°C, more preferably +10° to +50°C and at a pressure in the range 5 to 500 psia, more preferably 10 to 200 psia.

For isomerisation the amount of antimony on the catalyst is preferably from 1 to 25% by weight, more preferably from 5 to 15% by weight. Preferably the fluorinated alumina contains from 5 to 25% by weight of fluorine exclusive of that contained in the $SbF_5$.

For isomerisation it is found that increase in temperature increases the conversion. It is also found that under one atmosphere of hydrogen significant amounts of cracking and disproportionation occur. However the addition of cyclohexane or other naphthenes suppresses these unwanted side-reactions. It is preferred therefore to add from 1 to 10% by weight of a naphthene e.g. cyclohexane to the hydrocarbon feedstock.

Hydrogen fluoride may be added to the hydrocarbon feedstock in an amount less than 5% by weight in order to compensate for any hydrogen fluoride removed from the catalyst during the course of the reaction.

Preferably aromatic hydrocarbons, especially benzene are removed from the feedstock. Preferably the feed contains less than 0.1%, more preferably less than 0.01% by weight of aromatics.

According to another aspect of the present invention there is provided a process for the cracking of hydrocarbons which process comprises contacting a hydrocarbon feedstock with a solid acidic catalyst prepared by the process as hereinbefore described under cracking conditions.

Preferably the hydrocarbon feedstock is an n-paraffin or mixture of n-paraffins of carbon number 3 to 10 and the cracked product is an isoparaffin or mixture of isoparaffins. The preferred paraffin is n-pentane and the cracked product is isobutane.

Preferably the cracking is effected at a temperature in the range −20° to +100°C, even more preferably 10° to 70°C and a pressure of 5 to 500 psia, even more preferably 10 to 30 psia.

According to another aspect of the present invention there is provided a process for the alkylation of hydrocarbons which process comprises contacting a hydrocarbon feedstock with a solid acidic catalyst prepared by the process as hereinbefore described under alkylation conditions.

Preferably the hydrocarbon feedstock is a mixture of olefins of carbon number 2 to 6 and paraffins of carbon number 4 to 6.

Alkylation is preferably effected at a temperature in the range −40° to +50°C and at a pressure in the range 5 to 500 psia.

The invention is illustrated by the following Examples:

Catalyst Preparation

Example 1

Alumina (Sinclair-Baker RD 150 base) (10 g) was impregnated with a solution of boric acid (2.65 g) in water (25 ml). The solution was evaporated to dryness and the alumina dried at 110°C/18 $h$ and finally calcined in air and then in vacuo each at 450°C/3 $h$ to give an alumina-boria mixed oxide having an $Ho$ value of less than −8.2.

The catalyst was prepared by vaporizing antimony pentafluoride (0.9 ml) over the mixture of alumina and boria (10 ml) under vacuum at room temperature. 10 ml of catalyst were used in each of Examples 14 and 18.

Example 2

$Al_2O_3/B_2O_3$

The catalyst was prepared by vaporising 0.6 ml of $SbF_5$ as described in Example 1 over 10 ml of the alumina-boria prepared as described in Example 1.

Example 3

Silica (10 ml) was impregnated with a 20 percent wt aqueous solution of $SiO_2 12WO_3 . 26H_2O$ (20 ml). The solution was then evaporated to dryness and the silica dried at 110°C/18 h and finally calcined for 3 h at 200°C under vacuum to remove water of crystallization.

The product had an $Ho$ value of less than $-8.2$.

The heteropolyacid dispersed on the silica was impregnated with $SbF_5$ (0.9 ml) under vacuum as described in Example 1 before use.

Example 4

$SiO_2/NH_4F$

Silica (10 ml) was partially fluorided by impregnating with a solution of ammonium fluoride (10 percent wt) in water (25 ml). The solution was evaporated to dryness and the silica dried at 110°C/18 h and finally calcined at 450°C for 3 h under vacuum before use. Analysis of the product showed that it contained residual —OH groups. The product had an $Ho$ value of less than $-5.6$ but greater than $-8.2$.

The silica was impregnated with $SbF_5$ (0.9 ml) under vacuum as described in Example 1 before use.

Example 5

$Al_2O_3/HSO_3Cl$ (Eta) $\eta$-$Al_2O_3$ (12 ml) was heated in a stream of dry $N_2$ and then chlorosulphonic acid (8 ml) added dropwise from a syringe to the alumina at 540°C. Towards the end of the reaction white fumes of unreacted chlorosulphonic acid were detected in the $N_2$ stream at the outlet from the reactor. The alumina was then heated at 540°C in an $N_2$ stream for a further 3 hours. This reduced the chloride content of the base to about 0.1 percent weight.

% wt S = 5.45 : $Ho$ value $<-8.2$.

10 ml of this alumina was then contacted with antimony pentafluoride (2.5 ml) under vacuum. Residual antimony pentafluoride was removed by desorption under vacuum (<0.1 mm Hg) at room temperature until the sample reached constant weight.

% wt Sb = 11.3.

Example 6

$Al_2O_3/HF$ (Eta) $\eta$-alumina (Sinclair-Baker RD 150 : 50 ml) was soaked in 20 percent aqueous hydrofluoric acid (100 ml) for 20 minutes. The supernatant liquid was decanted off and the resulting fluorided alumina was dried on a steam bath and then heated in a stream of nitrogen for 3 hours at 540°C. The $Ho$ value was $<-8.2$.

Antimony pentafluoride was then contacted with the alumina and desorbed to constant weight as described in Example 5.

% wt Sb = 9.7.

Example 7

$NH_4$-Y-Zeolite/HF

Ammonium-exchanged Y-type zeolite (20 ml) was heated at 540°C in air for 5 hours. It was then soaked in 20 percent aqueous hydrofluoric acid (50 ml) for 30 minutes, the supernatant liquid decanted off, and dried on a steam bath, and then heated in a stream of nitrogen for 5 hours at 540°C. The $Ho$ value was $<-8.2$.

Antimony pentafluoride was added as described in Example 5.

% wt Sb = 17.4.

Example 8

$Al_2O_3/B_2O_3$

Alumina (Sinclair-Baker RD 150 : 10 g) was impregnated with a solution of boric acid (2.65g) in water 25 ml). The solution was evaporated to dryness and the solid dried at 110°C for 18 hours. The solid was calcined in air at 450°C/3 h and then heated in vacuum for 3 hours at 450°C. The $Ho$ value was $<-8.2$.

$SbF_5$ was then added as described in Example 5.

% wt Sb = 14.0.

Example 9

$Al_2O_3/B_2O_3HF$

The alumina-boria prepared as in Example 8 (10 ml) was soaked in 20 percent aqueous hydrofluoric acid (20 ml) for 20 minutes. The supernatant liquid was decanted off, the material dried on a steam bath and calcined in nitrogen at 540°C for 3 hours. The $Ho$ value was $<-8.2$.

% wt Sb = 9.8.

Example 10

$SiO_2/NH_4F$

Silica (12 g) was partially fluorided by impregnating with ammonium fluoride (1.2 g) in water (30 ml) and evaporating to dryness. The silica was dried at 110°C for 18 hours and finally calcined for 3 hours in nitrogen at 540°C. The $Ho$ value was between $-5.6$ and $-8.2$.

$SbF_5$ was then added as described in Example 5.

% wt Sb = 6.3.

Example 11 a. $Al_2O_3/SiO_2$

Sodium silicate (79 g) in water (about 250 ml) was added to aluminium sulphate (100 g) in water. The mixture was neutralized with aqueous ammonia and the resulting precipitate filtered, washed with ester and dried at 110°C for 18 hours. The product was calcined for 3 hours at 450°C in vacuo. The $Ho$ value was $<-8.2$.

$SbF_5$ was then added as described in Example 5.

% wt Sb = 20.0.

b. silica alumina containing 13% wt alumina (20 g 16–44 mesh) was fluorided by treatment with a solution of ammonium fluoride (8 g) in water (25 ml). The solution was evaporated to dryness, dried at 110°C for 8 hours and calcined in nitrogen for 3 hours at 540°C. The $Ho$ value was $<-8.2$.

$SbF_5$ was passed over as described in Example 5.

% wt Sb = 9.2.

Example 12

$V_2O_5/Al_2O_3/SO_2$ + air 10 percent $V_2O_5$ on alumina (obtained from Harshaw Chemical Company : 10 ml) was calcined in air at 500°C for 3 hours. The temperature was lowered to 400°C and then SO$_2$ and air were passed over the solid for 1 hour. The upper half of the bed had turned light green and the lower half a darker blue-green. The SO$_2$ and air were passed for a further 1 hour after which time the whole bed had turned light green.

The method of determining the H$o$ value of a support depends on colour and where the support is itself a coloured compound it is not possible to measure its H$o$ value.

% wt S = 3.1.

SbF$_5$ was then added as described in Example 5.

% wt Sb = 7.6.

Example 13

AlF$_3$

Aluminium fluoride was calcined at 540°C for 3 hours in nitrogen.

SbF$_5$ was then added as described in Example 5.

% wt. Sb = 5.2.

HYDROCARBON ISOMERISATION

Example 14

Use of catalyst prepared in Example 1 in liquid phase isomerisation of n-pentane to i-pentane.

Feed: Liquid pentane (n-pentane 93 percent; i-pentane 7 percent) containing 5 percent wt cyclohexane, and saturated with hydrogen at atmospheric pressure and room temperature.

The reaction was carried out at room temperature and atmospheric pressure.

| Flow rate LHSV | 1 vol/vol/hour |
|---|---|
| Conversion after 1 hour: | 45 per cent |
| Volatile Products: Isobutane | 2 per cent mol |
| n-pentane | 55 per cent |
| iso-pentane | 39 per cent |
| hexanes | 4 per cent |

The cyclohexane was added to reduce disproportionation and cracking reactions.

Example 15

The catalyst prepared in Example 2 was used for the vapour phase isomerisation of n-butane to i-butane.

Feed: n-Butane at GHSV of 120 v/v/h, N$_2$/H$_2$ mixture containing 10 percent mol H$_2$ at GHSV of 60 v/v/h.

The reaction was carried out at room temperature and atmospheric pressure

| Conversion after 15 minutes | 10 per cent |
|---|---|
| Products: n-butane | 90 per cent mol |
| iso-butane | 10 per cent mol |

Example 16

The catalyst prepared in Example 3 was used for the liquid phase isomerisation of n-pentane to i-pentane.

Conditions used were identical to those in Example 14.

| Conversion after 3 hours | 21 per cent |
|---|---|
| Volatile Products: n-pentane | 79 per cent mol |
| iso-pentane | 15 per cent |
| hexanes | 6 per cent |

Example 17

The catalyst prepared as described in Example 4 was used for the vapour phase isomerisation of n-butane to i-butane.

Conditions used were identical to those in Example 15.

| Conversion after 45 minutes: | 3 per cent |
|---|---|
| Products: n-butane | 97 per cent mole |
| iso-butane | 3 per cent |

HYDROCARBON CRACKING

Example 18

Use of catalyst prepared in Example 1 to crack a mixture of n-pentane and i-pentane.

Feed: N$_2$ and pentane (n-pentane 93 percent; i-pentane 7 percent) in molar ratio 2.8:1 (vapour phase).

Flow rate: 150 v/v/h. The reaction was carried out at room temperature and atmospheric pressure.

| Conversion after 15 minutes: | 99 per cent |
|---|---|
| Volatile products: iso-butane | 92 per cent mol |
| n-pentane | 1 per cent |
| iso-pentane | 7 per cent |

HYDROCARBON ISOMERISATION

Examples 19–28

The catalysts prepared as described in Examples 5 – 13 were tested for the isomerisation of n-pentane containing 5 percent weight of cyclohexane in Fischer and Porter glass pressure vessels (100 ml capacity) under 14 bar (ga) hydrogen pressure. 2 ml of catalyst and 20 ml of the pentane were stirred at 20°C for 2 hours. The products were then filtered off and analysed. The molar rates correspond to the number of moles of n-pentane converted per g atom of antimony per hour. The data are given in Table 1.

The results show that a number of oxides and mixed oxides can be used, but that partially sulphonated and fluorided aluminas give more active catalysts. Example 28 shows that catalysts derived from a completely fluorided alumina i.e. AlF$_3$ are inactive.

METHODS FOR PARTIALLY SULPHONATING ALUMINA

Example 29

(Eta) η-Al$_2$O$_3$ (15 ml) was heated at 540°C for 1 hour in a stream of dry air. A mixture of SO$_2$ and air were then passed over the catalyst at 540°C for 2 hours. The H$o$ value was less than −3.0.

% wt S = 4.4.

SbF$_5$ was then added as described in Example 5

% wt Sb = 13.2.

(continuation of the SO$_2$ and air treatment for a total of 6 hours gave a sulphur content of 4.9 percent weight).

Example 30

(Eta) $\eta$-$Al_2O_3$ (10 ml) was heated to 540°C in a stream of dry nitrogen. Liquid sulphur trioxide (ex Research Organic/Inorganic Chemical Corp; 6 ml) was added slowly at 540°C. The H$o$ value was less than −3.0.
% wt S = 8.4.
$SbF_5$ was then added as described in Example 5
% wt Sb = 11.8.

Example 31

(Eta) $\eta$-$Al_2O_3$ (10 ml) was heated to 540°C in a stream of dry nitrogen.. Fluorosulphonic acid (6 ml) was added slowly from a syringe to the alumina at 540°C. The H$o$ value was less than −3.0.
% wt. S = 14.5.
$SbF_5$ was then added as described in Example 5
% wt Sb = 0.8.

The catalysts prepared in Examples 29–31 were tested for n-pentane isomerisation as described for Examples 19–28. The data are given in Table 2.

Examples 29 to 31 illustrate different ways of effecting partial sulphonation of the alumina. The reason for the poor results using the fluorosulphonic acid is believed to be due to the destruction of the surface of the alumina.

USE OF AMMONIUM FLUORIDE AS FLUORINATING AGENT

Example 32

(Eta) $\eta$-alumina (20 g) was fluorided by contacting with a solution of ammonium fluoride (8 g) in water (50 ml) and evaporating to dryness. The fluorided alumina was dried at 110°C for 18 hours and then calcined under nitrogen at 540°C for 3 hours. The H$o$ value was <−8.2.
$SbF_5$ was then added as described in Example 5.
% wt Sb = 12.5.

The catalyst was tested for isomerisation of n-pentane under standard conditions. Data are given in Table 3.

This example shows that other fluorinating agents besides hydrofluoric acid can be used.

VARIATION IN BASE ALUMINA

Example 33

(Gamma) $\delta$-$Al_2O_3$ (15 ml) was heated at 540°C for 1 hour in dry air and then $SO_2$ and air were passed over for 2 hours at 540°C.
% wt S = 2.55.
The H$o$ value was less than −3.0.
$SbF_5$ was then added as described in Example 5.
% wt Sb = 12.7.

The catalyst was tested for n-pentane isomerisation and the data are given in Table 4.

This example shows that gamma alumina can be used to prepare the catalyst.

VARIATION IN DESORPTION TEMPERATURE

Examples 34–37

$SbF_5$ on partially sulphonated and fluorided alumina (prepared as described in Examples 5 and 6 respectively) were desorbed to constant weight in vacuo at different temperatures.

The catalysts were tested for the isomerisation of n-pentane under standard conditions. The data are given in Table 5.

These Examples show that the antimony pentafluoride is very strongly held to the surface of the alumina and since it cannot be removed by vacuum has probably reacted with the surface.

VARIATION IN CONTACTING AND DESORPTION PROCEDURES

Example 38

(eta) $\eta$-$Al_2O_3$ (10 ml) was heated at 540°C for 5 hours in dry nitrogen. $SbF_5$ (0.4 ml) was dissolved in dry liquid $SO_2$ (100 ml) and added slowly to the alumina. The $SO_2$ was allowed to boil off under a stream of nitrogen, and the catalyst was evacuated to constant weight at room temperature
Approximate % wt Sb = 9.

Example 39

Sulphonated alumina (prepared as described in Example 5; 10 ml) was heated at 540°C for 1 hour in a stream of $N_2$. $SbF_5$ (2 ml) was distilled on to the alumina and then the solid was washed with portions of dry liquid $SO_2$ (4 × 25 ml). The catalyst was then evacuated to constant weight.
% wt Sb = 5.2.

Example 40

Fluorided alumina (10 ml) prepared as described in Example 6 was reacted with $SbF_5$ as described in Example 39. Freon 113 (15 ml) was passed over the catalyst, which became hot. The word Freon is a registered trade mark. The Freon was drained off and a further 15 ml of Freon added. No exothermic reaction was noted on the second washing. Three further washings were carried out and then the catalyst was evacuated to constant weight.
% wt Sb = 11.5.

EXAMPLE 41

Fluorided alumina (containing approximately 20 percent weight fluorine and prepared from ammonium fluoride and $\eta$-alumina) (8.26 g) was impregnated with $SbF_5$ (4.39 g) in anhydrous liquid sulphur dioxide (approximately 100 ml). The product was desorbed to constant weight in vacuo at 100°C for 3 hours. Antimony content 10.4 percent weight.

The catalysts were then tested for the isomerisation of n-pentane under standard conditions. The data are given in Table 6.

These results show that excess $SbF_5$ may be removed by washing with liquid $SO_2$ or with Freon 113 to leave a catalyst still possessing isomerisation activity, but that impregnation of alumina with $SbF_5$ from $SO_2$ gives an inactive catalyst. However impregnation of partially fluorinated alumina with $SbF_5$ from $SO_2$ gives an active catalyst.

EFFECT OF SODIUM POISONING OF THE SUPPORT

Example 42

Fluorided alumina (prepared as described in Example 6; 10 ml) was contacted with $SbF_5$ as described in Example 1.
% wt Sb = 9.3.

Example 43

Fluorided alumina (prepared as described in Example 6; 10 ml) was added to sodium bicarbonate (2 g) in water (50 ml) and left to stand for 24 hours. Carbon dioxide was evolved slowly. The product was then filtered off, washed with water and heated in nitrogen for 3 hours at 540°C.

% wt Na = 1.0.

$SbF_5$ was then added as described in Example 5.

% wt Sb = 9.8.

Example 44

Alumina was sulphonated as described in Example 5, to give a product containing 9.1 percent weight sulphur. $SbF_5$ was then added as described in Example 5.

% wt Sb = 3.4.

Example 45

The alumina prepared as described in Example 5 (10 ml) was added to sodium bicarbonate (6.7g) in water (250 ml) and left to stand for 48 hours. Slow evolution of $CO_2$ was observed. The product was filtered off, washed with water, and heated in nitrogen for 3 hours at 540°C.

% wt S = 4.5.
% wt Na = 0.3.

$SbF_5$ was then added as described in Example 5
% wt Sb = 13.6.

These catalysts were tested for the isomerisation of n-pentane under standard conditions and the data are given in Table 7. These show that although only small amounts of sodium are present on the catalysts the activities have been substantially reduced. In the case of the sulphonated alumina, sodium bicarbonate treatment removes some of the sulphonate groups.

EFFECT OF PLATINUM ON CATALYTIC ACTIVITY

Example 46

Fluorided Pt on Alumina

A commercial platinum-on-alumina catalyst containing 0.38 percent weight platinum was fluorided with ammonium fluoride to give 4.5 percent weight fluorine. The Ho value was less than −3.0. The catalyst was calcined for 4 hours at 480°C in hydrogen and was then contacted with $SbF_5$ as described in Example 5.

% wt Sb = 10.2.

The catalyst was tested for the isomerisation of n-pentane to iso-pentane under standard conditions.

Conversion of n-pentane 46 percent mol. Molar rate 39.

This Example shows that the presence of platinum does not adversely affect the activity of the catalyst.

EFFECT OF REACTION CONDITIONS AND USE OF DIFFERENT FEEDSTOCKS

VARIATION OF REACTION CONDITIONS

Example 47

The data are given in Table 8. They indicate that an increase in temperature increases the reaction rate and the conversion of n-pentane under standard conditions.

Examples 48–52

The data are given in Table 9. They indicate that either a pressure of hydrogen or addition of 5 percent weight cyclohexane is necessary to prevent cracking and disproportionation reactions.

Examples 53–56

The data are given in Table 10. They show that increasing amounts of benzene in the feed lead to a reduction in the activity of the catalyst. In all cases, all the benzene was adsorbed on the catalyst. In example 55 the catalyst became yellow and 2 percent of iso-butane was detected in the products.

Other feeds

Example 57

A catalyst prepared from $SbF_5$ and partially fluorided alumina as described in Example 6 (containing 11.0 percent weight Sb) — 2 ml — was tested for the isomerisation of n-hexane (containing 5 percent weight cyclohexane) — 20 ml — at 20°C under 14 bar (ga) $N_2$ pressure for 2 hours.

Conversion of n-hexane 62% mol
Product contained
14.3% mol—2,2-dimethyl butane
33.7% mol—2-methyl pentane + 2,3-dimethyl butane
11.5% mol—3-methyl pentane
and a trace of cracked products.

Example 58

A catalyst prepared as described in Example 57 (2 ml) was tested for the isomerisation of cyclohexane (20 ml) at 20°C under 14 bar (ga) nitrogen for 2 hours.

Conversion of cyclohexane to methyl cyclopentane 10% mol.

Examples 59–63

In these examples, hydrogenated $C_5/C_6$ feedstock (containing <10 ppm benzene and dried over molecular sieve) — such as is used as a feed in conventional isomerisation reactors — was isomerised over a catalyst prepared from $SbF_5$ on partially fluorided alumina. The data are given in Table 11. For comparison between runs containing additional cyclohexane, cyclic products have been excluded from the analysis, i.e. non-cyclic products total 100 percent. The feedstock contained 2.1 percent mol methyl cyclopentane and 2.0 percent mol cyclohexane. The results show that:

1. Additional cyclohexane does not affect the activity of the catalyst
2. Increase in temperature increases the conversion, but small amounts of iso-butane were detected.
3. Addition of n-amyl fluoride had a detrimental effect on the catalyst activity.

CONTINUOUS FLOW CONDITIONS

Example 64

Table 12 gives the data for the isomerisation of n-butane over an $SbF_5$-sulphonated alumina catalyst prepared as described in Example 29 in a flow reactor at atmospheric pressure.

Example 65

Table 13 gives the data for isomerisation of n-pentane (containing 5 percent weight cyclohexane and saturated with $H_2$ at atmospheric pressure) over an $SbF_5$ — partially fluorided alumina, prepared as described in Example 6, catalyst at 22°C at atmospheric pressure.

Example 66

Table 14 gives the data for isomerisation of hydrogenated $C_3/C_6$ feedstock (the same feed as used in examples 59–63) using an $SbF_5$ on partially fluorided alumina catalyst prepared as described in Example 6 at atmospheric pressure at 22°C.

Example 67

(Eta) η-alumina (16 ml : 16–44 mesh) was immersed in a solution of ammonium fluoride (2g) in water (25 ml). The solution was evaporated to dryness, and dried at 110°C for 18 hours, and then calcined in vacuo at 450°C for 2 hours. This procedure was repeated except the final calcination was for 3 hours. The H$o$ value was less than −8.2.

The partly fluorided alumina (6.7 g) was added to hexafluoroantimonic acid (6.9 g) in a Teflon bottle. 1.5 ml of this material, which had a dry appearance, was added to n-pentane (10 ml) containing 5 percent of cyclohexane. The test was carried out in a glass pressure vessel at 20°C for 2 hours under 14 bar (ga) hydrogen pressure.

Sb content of catalyst 25% wt.
Conversion of n-pentane 56% mol
Molar rate 6

This example illustrates that catalysts prepared by depositing hexafluoroantimonic acid on fluorided alumina are less active than those derived from antimony pentafluoride.

ALKYLATION

ALKYLATION OF ISOBUTANE WITH PROPYLENE

Examples 68–73

η-alumina (166 g) was partially fluorided by contacting the solid with a solution of ammonium fluoride (66g) in water (200ml) and evaporating to dryness. The alumina was then calcined in nitrogen for 3 hours at 540°C. The fluorine content was approximately 20% wt. The H$o$ value was <−8.2.

The partially fluorided alumina (20 ml) was heated to 100°C under vacuum and then antimony pentafluoride (2ml) passed over in the vapour phase. The excess of antimony pentafluoride was desorbed at 100°C in vacuo until no further loss in weight occurred The catalyst contained 7.3% wt of antimony.

A sample of the catalyst (0.6g) was loaded into a 100 ml glass pressure vessel in a dry box. Iso-butane (15g) was condensed into the vessel, which was cooled in ice, and then propylene (1.75g) added to the mixture in portions over 2 hours. A pressure of hydrogen of 3.5 bar (ga) was maintained throughout. At the end of the reaction time the vessel was weighed, and then the liquid product decanted from the catalyst and analysed. The results are given in Table 15.

The analysis of the $C_7$ fraction in Example 70 was as follows:

| | |
|---|---|
| 2,2-dimethylpentane | 0.7% mol |
| 2,4-dimethylpentane | 24.5 |
| 2,2,3-trimethylbutane | 0.3 |
| 3,3-dimethylpentane | 1.3 |
| 2-methylhexane | 4.3 |
| 2,3-dimethylpentane | 65.2 |
| 3-methylhexane | 3.5 |
| 3-ethylpentane | 0.1 |
| n-pentane | 0.1 |
| | 100.0 |

The results from examples 68–70 show that a higher yield of alkylate is obtained if the olefin is added in several portions.

The results from examples 71–73 show that the maximum yield of alkylate was obtained at 20°C.

ALKYLATION OF ISOBUTANE WITH ETHYLENE

Examples 74–77

The catalyst was prepared as described in example 68 and contained 7.8% wt of antimony. The H$o$ value was less than −8.2. In examples 74–77 ethylene (1.2g) was added in 4 portions over one hour, under a pressure of hydrogen of 3.5 bar (ga). In example 77 ethylene (2.3 g) was added in eight portions over 1 hour.

The results are shown in Table 16.

The analysis of the $C_6$ fraction in Example 75 was as follows:

| | |
|---|---|
| 2,2-dimethylbutane | 32.1% mol |
| 2,3-dimethylbutane | 47.5 |
| 2-methylpentane | 14.0 |
| 3-methylpentane | 6.2 |
| n-hexane | 0.2 |
| | 100.0 |

Examples 74–76 show that with ethylene the maximum yield of alkylate was obtained at −20°C. Example 77 shows that doubling the amount of olefin gave almost double the olefin yield. (The overall isoparaffin: olefin ratio in this case was approximately 3.5 : 1).

ALKYLATION OF ISOBUTANE WITH BUTENE-2

Examples 78–82

The catalyst was prepared as described in example 68 and contained 7.8% wt of antimony. The H$o$ value was less than −8.2.

In examples 78–80, butene-2 (2.3g) was added in 4 portions over one hour under a pressure of hydrogen 3.5.bar (ga). In examples 81–82 the reaction was carried out under a pressure of nitrogen of 10.5 bar(ga). In example 81, butene-2 (2.3g) was added in 4 portions over 1 hour. In example 82, butene-2 (4.6g) was added in 8 portions over 1 hour.

The results are given in Table 17. The analysis of the $C_8$ fraction of the product from example as follows:

| | |
|---|---|
| 2,2,4-trimethylpentane | 32.6 % mol |
| 2,2-dimethylhexane | 1.6 |
| 2,5-dimethylhexane | 9.0 |
| 2,2,3-trimethylpentane } 2,4-dimethylhexane } | 18.4 |
| 3,3-dimethylhexane | 0.4 |
| 2,3,4-trimethylpentane | 14.9 |
| 2,3,3-trimethylpentane | 13.7 |
| 2,3-dimethylhexane } 3-ethyl-2-methylpentane } | 3.8 |
| 2-methylheptane | 1.9 |
| 4-methylheptane | 0.3 |
| 3-ethyl-3-methylpentane } 3,4-dimethylhexane } 3-methylheptane } | 0.9 |
| 3-ethylhexane } n-octane } | 2.5 |
| | 100.0 |

ISOMERISATION OF N-PENTANE

Example 83 a. An $SbF_5$ on partially fluorided alumina containing 10.0 percent weight of antimony (Ho value <−8.2) and prepared by vapour phase impregnation of $SbF_5$ was tested under the conditions of Example 41 for the isomerisation of n-pentane containing 5 percent of cyclohexane.

Conversion of n-pentane 50 percent
Molar rate 36 b. A second sample of the above catalyst was treated with excess of iso-butane and then the iso-butane evaporated off. The material was tested for the isomerisation of n-pentane (with no added cyclohexane).

Conversion of n-pentane 65 percent
Molar rate 43

This example demonstrates that pretreatment of the catalyst with iso-butane enchances its activity, although small amounts of cracking and disproportionation were also detected.

VARIATION OF FLUORIDE CONTENT

Example 84

These examples demonstrate the effect of varying the fluoride content of the alumina support on the activity of the antimony catalysts. The data are detailed in Table 18. Isomerisation conditions were the same as those in Example 41.

These results show that the fluorine content of the alumina over the range 7–42 percent weight does not dramatically affect the molar rate, although the amount of antimony bound to the catalyst decreases as the fluoride content increases.

Examples 7, 11a, 13, 25, 28 and 67 are not Examples according to the invention.

TABLE 2
VARIATION OF SULPHONATION PROCEDURE ON η(ETA) $Al_2O_3$

| Ex. No. | Sulphonating Agent | Antimony Content (% wt) | Sulphur Content (% wt) | Conversion of n-pentane (% mol) | Molar Rate |
|---|---|---|---|---|---|
| 19 | $HSO_3Cl$ | 11.3 | 5.5 | 60 | 31 |
| 29 | $SO_2$-air | 13.2 | 4.2 | 68 | 25 |
| 30 | $SO_3$ | 11.8 | 8.4 | 57 | 25 |
| 31 | $HSO_3F$ | 0.8 | 14.5 | 2 | 9 |

TABLE 3
VARIATION OF FLUORIDING PROCEDURE ON $η-Al_2O_3$

| Ex. No. | Fluoriding Agent | Antimony Content (% wt) | Conversion n-pentane (% mol) | Molar Rate |
|---|---|---|---|---|
| 20 | HF | 9.7 | 55 | 33 |
| 32 | $NH_4F$ | 12.5 | 58 | 26 |

TABLE 4
VARIATION IN BASE ALUMINA (SULPHONATED USING $SO_2$ AND AIR)

| Ex. No. | Base Alumina | Antimony Content (% wt) | Sulphur Content (% wt) | Conversion of n-pentane (% mol) | Molar Rate |
|---|---|---|---|---|---|
| 29 | $η-Al_2O_3$ | 13.2 | 4.2 | 68 | 25 |
| 33 | $γ-Al_2O_3$ | 12.7 | 2.6 | 58 | 21 |

TABLE 5
VARIATION IN DESORPTION TEMPERATURE

| Ex. No. | Support | Desorption Temp (°C) | Antimony Content (% wt) | Conversion of n-pentane (% mol) | Molar Rate |
|---|---|---|---|---|---|
| 34 | $Al_2O_3$/$HSO_3Cl$ | 20 | 8.8 | 57 | 30 |
| 35 | $Al_2O_3$/$HSO_3Cl$ | 50 | 8.6 | 53 | 29 |
| 20 | $Al_2O_3$/HF | 20 | 12.6 | 59 | 27 |
| 36 | '' | 120 | 8.8 | 34 | 23 |
| 37 | '' | 200 | 8.1 | 0 | 0 |

TABLE 1
VARIATION OF SUPPORT

| Catalyst Preparation Example No. | Example No. | Support | Antimony Content (% wt) | Conversion of n-pentane (% mol) | Molar Rate (mol pentane converted/g-atom Sb/h) |
|---|---|---|---|---|---|
| 5 | 19 | $Al_2O_3$/$HSO_3Cl$ | 11.3 | 60 | 31 |
| 6 | 20 | $Al_2O_3$/HF | 9.7 | 55 | 33 |
| 7 | 21 | $NH_4$-Y-Zeolite/HF | 17.4 | 4 | 2 |
| 8 | 22 | $Al_2O_3$/$B_2O_3$ | 14.0 | 28 | 11 |
| 9 | 23 | $Al_2O_3$/$B_2O_3$/HF | 9.8 | 8 | 5 |
| 10 | 24 | $SiO_2$/$NH_4F$ | 6.3 | 2 | 4 |
| 11(a) | 25 | $Al_2O_3$/$SiO_2$ | 20.0 | 0 | 0 |
| 11(b) | 26 | $Al_2O_3$/$SiO_2$/$NH_4F$ | 9.2 | 7 | 9 |
| 12 | 27 | $V_2O_5$/$Al_2O_3$/$SO_2$-air | 7.6 | 16 | 10 |
| 13 | 28 | $AlF_3$ | 5.2 | 0 | 0 |

TABLE 6
VARIATION OF IMPREGNATION AND DESORPTION PROCEDURES

| Example No. | Support | Impregnation Procedure | Desorption* Procedure | Antimony Content (% wt) | Conversion of n-pentane (% mol) | Molar Rate |
|---|---|---|---|---|---|---|
| 38 | $Al_2O_3$ | Solution in Liquid $SO_2$ | Evacuation | 5.2 | 0 | 0 |
| 39 | $Al_2O_3$/$HSO_3Cl$ | Vapour Phase | Wash with liquid $SO_2$ | 5.2 | 25 | 25 |

TABLE 6-continued

VARIATION OF IMPREGNATION AND DESORPTION PROCEDURES

| Example No. | Support | Impregnation Procedure | Desorption* Procedure | Antimony Content (% wt) | Conversion of n-pentane (% mol) | Molar Rate |
|---|---|---|---|---|---|---|
| 40 | $Al_2O_3$/HF | Vapour Phase | Wash with Freon 113 | 11.5 | 13 | 6 |
| 41 | $Al_2O_3$/$NH_4F$ | Solution in Liquid $SO_2$ | Evacuation | 10.4 | 47 | 26 |

*Final evacuation to constant weight to remove excess of washing liquid carried out in all cases.

TABLE 7

EFFECT OF SODIUM POISONING OF SUPPORT

| Ex. No. | Support | % wt Sodium | % wt Sulphur | % wt Antimony | Conversion of n-pentane (% mol) | Molar Rate |
|---|---|---|---|---|---|---|
| 42 | $Al_2O_3$/HF | — | — | 9.3 | 53 | 23 |
| 43 | " | 1.0 | — | 9.8 | 31 | 17 |
| 44 | $Al_2O_3$/$HSO_3Cl$ | — | 9.1 | 3.4 | 32 | 35 |
| 45 | " | 0.3 | 4.5 | 13.6 | 13 | 4 |

TABLE 8

VARIATIONS IN REACTION TEMPERATURES

| Ex. No. | Support | Reaction Temp (°C) | % wt Antimony | Conversion n-pentane (% mol) | Molar Rate |
|---|---|---|---|---|---|
| 32 | $Al_2O_3$/$NH_4F$ | 20 | 12.5 | 58 | 26 |
| 47 | " | 40 | 12.5 | 70 | 31 |

The Ho value of the fluorinated alumina was less than −8.2

TABLE 10

EFFECT OF BENZENE
(SUPPORT — $Al_2O_3$/HF; Ho VALUE <−8.2)

| Example No. | ppm Benzene | Conversion of n-pentane (% mol) | Molar Rate |
|---|---|---|---|
| 53 | 0 | 55 | 27 |
| 54 | 130 | 46 | 26 |
| 55 | 260 | 44 | 24 |
| 56 | 520 | 31 | 18 |

TABLE 9

EFFECT OF REACTION CONDITIONS ON CONVERSION
(SUPPORT — $Al_2O_3$/HF: Ho value <−8.2)

| Example No. | % weight Antimony | Atmosphere | Pressure (bar (ga)) | % wt cyclohexane added | Conversion (% mol) | Molar Rate | Other Products |
|---|---|---|---|---|---|---|---|
| 48 | 8.6 | $H_2$ | 0 | 0 | 36 | 25 | iso-butane 7% $C_6$ products 3% |
| 49 | 8.6 | $H_2$ | 0 | 5 | 40 | 25 | trace $^iC_4$ |
| 50 | 8.6 | $H_2$ | 14 | 0 | 42 | 28 | — |
| 51 | 12.1 | $H_2$ | 14 | 5 | 54 | 26 | — |
| 52 | 12.1 | $N_2$ | 14 | 5 | 57 | 27 | — |

TABLE 11

ISOMERISATION OF $C_5$/$C_6$ FEEDSTOCK
Catalyst: $SbF_5$ on $Al_2O_3$/HF prepared as described in Example 6
Pressure: 14 bar (ga) $H_2$

| Example No. | Antimony Content (% wt) | Temp (°C) | Added Component | Amount of added Component | $^iC_4$ | $^iC_5$ | $^nC_5$ | 22 DMB | 2 MP 23 DMB | 3 MP | $^nC_6$ |
|---|---|---|---|---|---|---|---|---|---|---|---|
| Feedstock | — | — | — | — | — | 20.6 | 29.4 | 0.7 | 19.2 | 11.3 | 18.8 |
| 59 | 10.8 | 20 | — | — | — | 26.9 | 20.5 | 13.9 | 22.0 | 6.8 | 9.8 |
| 60 | 10.8 | 20 | Cyclohexane | 5% weight | — | 26.7 | 20.9 | 14.1 | 22.0 | 6.8 | 9.6 |
| 61 | 14.2 | 20 | — | — | — | 31.4 | 17.0 | 21.0 | 19.8 | 5.6 | 5.2 |
| 62 | 14.2 | 55 | — | — | 1.2 | 36.7 | 9.9 | 22.2 | 20.4 | 6.3 | 3.5 |
| 63 | 14.2 | 20 | n-amyl fluoride | 0.2 ml | 2.2 | 27.8 | 21.0 | 9.3 | 23.7 | 6.3 | 9.6 |

*Analysis excluding cyclic products (cyclohexane and methyl cyclopentane)

ABBREVIATIONS
DMB = dimethyl butane
MP = methyl pentane
n-$C_6$ = n-hexane
n-$C_5$ = n-pentane
i-$C_5$ = iso-pentane
i-$C_4$ = iso-butane
n-$C_4$ = n-butane

TABLE 12

EXAMPLE 64
ISOMERISATION OF n-BUTANE

Catalyst: SbF$_5$ on Al$_2$O$_3$/SO$_2$+air prepared as described in Example 29
% wt Sb = 14.8; % wt S = 4.9; Ho value <−3.0

Conditions: Catalyst bed 8 ml
CHSV = 60

| Time (minutes) | Temperature (°C) | Product analysis (% mol) | | | |
|---|---|---|---|---|---|
| | | <C$_4$ | $^i$C$_4$ | $^n$C$_4$ | $^i$C$_5$ |
| 32 | 20 | 0 | 2.7 | 97.3 | 0 |
| 115 | 65 | 14.5 | 48.8 | 36.8 | trace |
| 220 | 50 | 6.4 | 47.7 | 45.9 | trace |
| 320 | 50 | 4.7 | 45.3 | 48.6 | 1.3 |

TABLE 13

EXAMPLE 65
ISOMERISATION OF n-PENTANE

Catalyst: SbF$_5$ on Al$_2$O$_3$/HF
% wt Sb = 11.0

Conditions: Catalyst bed 17 ml
Temperature: 22°C

| Time (minutes) | LHSV | Product Analysis (% mol) | | | |
|---|---|---|---|---|---|
| | | $^i$C$_4$ | $^i$C$_5$ | $^n$C$_5$ | C$_6$ |
| 75 | 1.3 | 3.4 | 77.3 | 19.3 | trace |
| 225 | 1.3 | 1.3 | 69.3 | 29.4 | trace |
| 285 | 1.4 | 0 | 62.7 | 37.3 | 0 |
| 345 | 0.7 | 0 | 68.2 | 31.8 | 0 |

TABLE 14

EXAMPLE 66
ISOMERISATION OF C$_5$/C$_6$ FEEDSTOCK

Catalyst: SbF$_5$ on Al$_2$O$_3$/HF
% wt Sb = 12.3

Conditions: Catalyst bed 20 ml
Temperature: 22°C
LHSV = 1

| Time (minutes) | Product Analysis (% mol) | | | | | | |
|---|---|---|---|---|---|---|---|
| | $^i$C$_4$ | $^i$C$_5$ | $^n$C$_5$ | 22 DMB | 23 DMB 2 MP | 3 MP | $^n$C$_6$ |
| 90 | 11.1 | 33.4 | 10.1 | 22.6 | 16.3 | 3.3 | 3.4 |
| 180 | 3.3 | 30.5 | 16.5 | 13.5 | 22.9 | 6.0 | 7.3 |

TABLE 15

| ALKYLATIONS WITH PROPYLENE | | | | | | | | |
|---|---|---|---|---|---|---|---|---|
| Example No. | No. of additions of propylene (total 1.75g) | Temp °C | Wt of Alkylate (g) | Analysis of alkylate — Composition of C$_5$ – C$_8$ fraction (% mol) | | | | Fraction >C$_8$ as % of total alkylate |
| | | | | C$_5$ | C$_6$ | C$_7$ | C$_8$ | |
| 68 | 2 | 0 | 0.6 | (not determined) | | | | 75.8 |
| 69 | 4 | 0 | 1.7 | 3.1 | 4.2 | 82.1 | 10.4 | 16.8 |
| 70 | 8 | 0 | 2.5 | 2.8 | 3.1 | 87.6 | 6.5 | 13.6 |
| 71 | 4 | −20 | 0.4 | (not determined) | | | | (not determined) |
| 72 | 4 | 0 | 1.4 | 3.4 | 4.4 | 78.8 | 13.4 | 24.2 |
| 73 | 4 | +20 | 2.7 | 6.0 | 6.4 | 77.4 | 10.2 | 16.5 |

TABLE 16

| ALKYLATIONS WITH ETHYLENE | | | | | | | |
|---|---|---|---|---|---|---|---|
| Example No. | Temp °C | Wt of Alkylate (g) | Analysis of C$_5$ – C$_8$ fraction of alkylate (% mol) | | | | Fraction >C$_8$ as % of total alkylate |
| | | | C$_5$ | C$_6$ | C$_7$ | C$_8$ | |
| 74 | −20 | 2.1 | 2.3 | 69.7 | 1.3 | 26.7 | 7.6 |
| 75 | 0 | 1.8 | 4.8 | 72.4 | 3.4 | 19.4 | 8.2 |
| 76 | +20 | 1.4 | 4.4 | 67.8 | 4.6 | 23.2 | 7.6 |
| 77 | 0 | 3.5 | 3.6 | 60.2 | 3.5 | 32.7 | 10.8 |

TABLE 17

| ALKYLATIONS WITH BUTENE-2 | | | | | | | |
|---|---|---|---|---|---|---|---|
| Example No. | Temp °C | Wt of Alkylate (g) | Analysis of C$_5$ – C$_8$ fraction of alkylate (% mol) | | | | Fraction >C$_8$ as % of total alkylate |
| | | | C$_5$ | C$_6$ | C$_7$ | C$_8$ | |
| 78 | −20 | 1.1 | 0.6 | 1.5 | 2.0 | 95.9 | 45.6 |
| 79 | 0 | 2.2 | 4.6 | 4.2 | 5.5 | 85.7 | 18.2 |
| 80 | +20 | 1.6 | 0.3 | 6.4 | 17.5 | 75.8 | 34.0 |
| 81 | 0 | 3.9 | 4.3 | 3.6 | 4.9 | 87.2 | 27.6 |
| 82 | 0 | 5.1 | 4.1 | 3.3 | 4.6 | 88.0 | 27.6 |

TABLE 18

| Example No. | % F on $Al_2O_3$ | % Sb in Catalyst | Conversion of n-pentane | Molar Rate |
|---|---|---|---|---|
| 84(a) | 5.3 | 16.3 | 64 | 24 |
| 84(b) | 7.7 | 11.5 | 60 | 37 |
| 84(c) | 20* | 10.0 | 50 | 36 |
| 84(d) | 42.0 | 6.35 | 34 | 37 |

*Approximate fluoride content. Same catalyst as that described in Example 83(a).

We claim:

1. A process for the production of a solid acidic catalyst suitable for use in hydrocarbon conversion reactions which process consists essentially of reacting antimony tetrafluoride at a temperature in the range of −50° to +140°C. with an inorganic oxide selected from the group consisting of silica, alumina, boria, and mixtures thereof, said inorganic oxide or mixture thereof having surface hydroxyl groups and an Ho value of less than −3.0.

2. A process for the production of a solid acidic catalyst suitable for use in hydrocarbon conversion reactions which process consists essentially of reacting a compound of formula $XF_5$ wherein X is a metal selected from the group consisting of arsenic, antimony, bismuth, tantalum, vanadium and niobium at a temperature in the range of −50° to +140°C. with an inorganic oxide derived from a silico-tungstic acid on a silica support by impregnating the silica with a solution of the acid followed by drying and then heating to drive off the water of crystallisation, said inorganic oxide having surface hydroxyl groups and an Ho value of less than −3.0.

3. A process for the production of a solid acidic catalyst suitable for use in hydrocarbon conversion reactions which process consists essentially of reacting a compound of formula $XF_5$ wherein X is a metal selected from the group consisting of arsenic, antimony, bismuth, tantalum, vanadium and niobium at a temperature in the range of −50° to +140°C. with an inorganic oxide selected from the group consisting of silica, alumina, boria, and mixtures thereof, said inorganic oxide or mixture thereof having surface hydroxyl groups and an Ho value of less than −3.0, the inorganic oxide being partially fluorinated by reaction with a fluorinating agent before reaction with the compound of formula $XF_5$.

4. A process for the production of a solid acidic catalyst suitable for use in hydrocarbon conversion reactions which process consists essentially of reacting a compound of formula $XF_5$ wherein X is a metal selected from the group consisting of arsenic, antimony, bismuth, tantalum, vanadium and niobium at a temperature in the range of −50° to +140°C. with an inorganic oxide selected from the group consisting of silica, alumina, boria, and mixtures thereof, said inorganic oxide or mixture thereof having surface hydroxyl groups and an Ho value of less than −3.0, the inorganic oxide being partially sulphonated by reactions with a sulphonating agent before reaction with the compound of formula $XF_5$.

5. A process for the production of a solid acidic catalyst suitable for use in hydrocarbon conversion reactions which process consists essentially of reacting a compound of formula $XF_5$ wherein X is a metal selected from the group consisting of arsenic, antimony, bismuth, tantalum, vanadium and niobium, at a temperature in the range of −50° to +140°C. with alumina having surface hydroxyl groups and which is reacted with sufficient of an agent selected from the group consisting of a fluorinating agent and sulphonating agent to partially fluorinate or sulphonate the alumina and wherein the unreacted fluorinating or sulphonating agent is removed before reacting the partially fluorinated or sulphonated alumina with the compound of formula $XF_5$ and said alumina having an Ho value of less than −3.0.

6. A process according to claim 5 wherein the fluorinating agent is selected from the group consisting of hydrogen fluoride and ammonium fluoride.

7. A process according to claim 5 wherein the sulphonating agent is selected from the group consisting of chlorosulphonic acid ($HSO_3Cl$), sulphur dioxide in admixture with air and sulphur trioxide.

8. A process according to claim 5 wherein after removing any unreacted fluorinating or sulphonating agent and prior to reacting the alumina with the compound of formula $XF_5$ the partially fluorinated or sulphonated alumina is treated with nitrogen at a temperature in the range 300° to 800°C. for a period of 1 to 8 hours.

9. A process according to claim 5 wherein the alumina prior to reaction with $XF_5$ compound is mixed with an inorganic oxide selected from the group consisting of boria and silica.

10. A process according to claim 5 wherein the extent of fluorination is such that the alumina contains from 1 to 45% by weight of fluorine.

11. A process according to claim 10 wherein the alumina contains from 1 to 25% by weight of fluorine.

12. A process according to claim 5 wherein the extent of sulphonation is such that the alumina contains from 1 to 20% by weight of sulphur.

13. A process according to claim 1 wherein the Ho value of the inorganic oxide is less than −8.0.

14. A process according to claim 1 wherein any excess of the compound $XF_5$ is removed from the inorganic oxide.

* * * * *